(12) United States Patent
Kaufman

(10) Patent No.: US 8,668,920 B2
(45) Date of Patent: *Mar. 11, 2014

(54) METHOD, DEVICE, AND SYSTEM FOR DELIVERY OF THERAPEUTIC AGENTS TO THE EYE

(75) Inventor: Herbert Edward Kaufman, Sarasota, FL (US)

(73) Assignee: HEK Development, LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/494,252

(22) Filed: Jun. 12, 2012

(65) Prior Publication Data

US 2012/0253300 A1 Oct. 4, 2012

Related U.S. Application Data

(63) Continuation of application No. 12/226,963, filed as application No. PCT/US2007/010981 on May 4, 2007, now Pat. No. 8,216,603.

(60) Provisional application No. 60/797,533, filed on May 4, 2006.

(51) Int. Cl.
*A61F 2/00* (2006.01)

(52) U.S. Cl.
USPC .......................................... 424/428; 514/912

(58) Field of Classification Search
USPC .......................................... 424/428; 514/912
See application file for complete search history.

(56) References Cited

U.S. PATENT DOCUMENTS

| 3,811,444 | A * | 5/1974 | Heller et al. .................. 424/428 |
| 2002/0107508 | A1 * | 8/2002 | Burnett ............................. 606/5 |
| 2005/0046794 | A1 | 3/2005 | Silvestrini et al. |

* cited by examiner

*Primary Examiner* — Zohreh Fay
(74) *Attorney, Agent, or Firm* — Brinks Gilson & Lione

(57) ABSTRACT

A method, device, and system for easier, consistent, and comfortable delivery of therapeutic agents to the front of the eye.

12 Claims, 3 Drawing Sheets

METHOD, DEVICE, AND SYSTEM FOR DELIVERY OF THERAPEUTIC AGENTS TO THE EYE

PRIORITY INFORMATION

This application is a continuation Application of U.S. application Ser. No. 12/226,963, filed Feb. 18, 2009, the entire contents of which is hereby incorporated herein by reference. U.S. application Ser. No. 12/226,963 is a National Stage application of International Application No. PCT/US2007/010981, filed May 4, 2007, which claims the benefit of U.S. Provisional Application No. 60/797,533, filed May 4, 2006, the entire contents of which are hereby incorporated herein by reference.

BACKGROUND OF THE INVENTION

There are many ocular disorders that require treatment by the application of therapeutic agents to the front of the eye. For example, glaucoma is the second most common cause of blindness in the United States. About two million Americans have glaucoma, and only about half of those patients with glaucoma are aware of it because the disease is generally asymptomatic. Because of the asymptomatic nature of the disease, patients often have trouble complying with glaucoma therapy. Adding to patient compliance issues is the need to apply eye drops to the front of the eye, which will decrease the ocular pressure in the eyes of glaucoma patients. Many patients simply have trouble applying drops to their eyes.

Other ocular disorders requiring the application of therapeutic agents to the front of the eye include keratitis sicca, corneal ulcers (bacterial and viral), conjunctivitis, and allergies. Each of these disorders, as well as others, require the application of artificial tears, ointments, antibiotics, and/or antiviral agents to the front of the eye to be treated adequately. In addition, patients who are post-ocular surgery often need to prevent post-surgical infection or inflammation by applying anti-inflammatory agents and antibiotics to the front of the eye. Like many glaucoma patients, patients affected by the foregoing disorders often have difficulty complying with treatment because of difficulty applying therapeutic agents or eye drops to the front of the eye.

What is needed is a method, system, and device whereby patients with ocular disorders may comply with treatment requiring the application of therapeutic agents to the front of the eye. What is needed is a method, system, and device whereby patients with ocular disorders can routinely and consistently have medications applied to their eyes without any difficulty, fear, or discomfort of placing eye drops or other medications in their eyes.

BRIEF SUMMARY OF THE INVENTION

Accordingly, it is an object of this invention is to provide a method, device, and system for easier, comfortable, and more consistent delivery of opthalmic therapeutic agents to the front of the eye by allowing a physician to place a drug delivery device in the patient's eye.

The present invention relates to a device containing therapeutic agents. The device may be inserted by a physician or eye care professional, rather than by a patient, which will allow the therapeutic agents to be applied to the eye without patient anxiety about inserting eye drops in the eye. Upon insertion, the device will be placed around the entire circumference of the cornea rather than simply being placed in the lower fornix of the eye. After insertion, the device will be comfortable. In the preferred embodiment of the invention, the inner diameter of the device would be 13-19 mm and the width of the device measured on the external edges will measure 1-5 mm.

The device may be inserted into a patient's eye on either a long-term (3-6 months) or a short-term basis. After the therapeutic agents in the device are depleted and effective agents are no longer being liberated by the device, a patient may return to his/her physician for insertion of a new device or for replenishment of the device with additional therapeutic agents. The device may be totally biodegradable, and if short-term treatment is necessary, a biodegradable device may not be replaced. If long-term treatment is necessary, a biodegradable device may either be replaced or replenished with additional therapeutic agent(s). If the therapeutic agent is a solution or crystalline drug, a drug delivery limiting membrane such as polyvinyl alcohol may be placed on the device. The device may be used in conjunction with contact lenses and other ocular appliances.

BRIEF DESCRIPTION OF THE DRAWINGS

A full and enabling disclosure of the present invention, including the best mode thereof, to one of ordinary skill in the art, is set forth more particularly in the remainder of the specification including reference to the accompanying drawing in which.

DETAILED DESCRIPTION OF THE INVENTION

Figure 1:
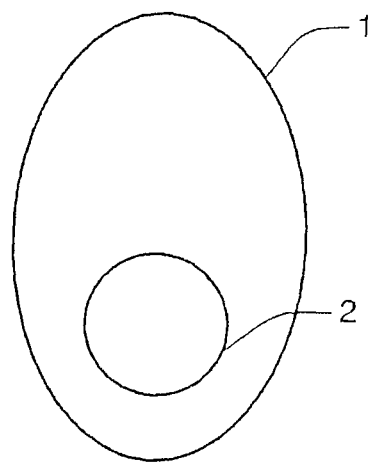
FIG. 1 depicts the top view of the device having an elliptical outer edge and an inner edge that is circular in shape.
Figure 2:
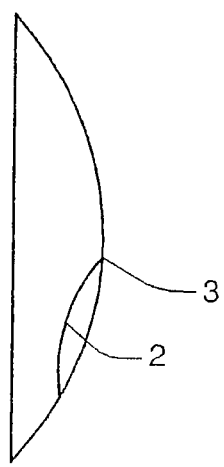
FIG. 2 depicts the side view of the device having an elliptical outer edge and an inner edge that is circular in shape.
Figure 3:
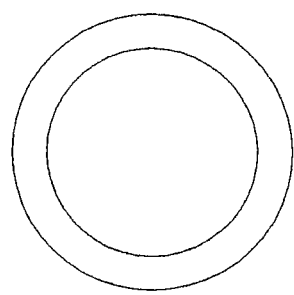
FIG. 3 depicts the top view of the device having a toric shape.

One embodiment of the invention is a device having an outer edge that is elliptical in shape 1 and an inner edge that is circular in shape 2. In another embodiment of the invention, the device is toric in shape. In yet another embodiment of the invention, the device is C-shaped.

The device may have a barrier membrane along all or part of the device. One or more therapeutic agents are incorporated into the barrier membrane allowing therapeutic agents to be applied to the front of the eye. The amount of therapeutic agents delivered to the front of the eye may be varied by varying the dimensions of the barrier membrane. The dimensions of the device may range from 13-19 mm in the inner diameter and 1-5 mm in width measured on the outer edges of the device. The device may be composed of a soft or rigid polymer. In yet another embodiment of the invention, the outer edge of the device may be composed partially or entirely of metal to provide structural support for the device.

In another embodiment of the invention, the device may be used by being placed along the outer edge of a contact lens or made a part of a contact lens. In this embodiment of the invention, the inner diameter and width of the device will vary depending upon the contact lens with which the device is used.

If a therapeutic agent is incorporated in a barrier membrane along all or part of the device is soluble or crystalline, the device may include a delivery limiting membrane such as polyvinyl alcohol.

In another embodiment of the invention, the device is convex in shape. In a preferred embodiment of the invention, the apex of the convexity 3 of the device touches the inner circular edge of the device.

In another embodiment of the invention, the device is combined with one or more therapeutic agents. The therapeutic agents may be precipitated within the polymer of which the device may be composed. The therapeutic agents will dissolve or hydrolyze such that they will be delivered into the fluid bathing the front of the eye.

In yet another embodiment of this invention, the device is composed of a biodegradable polymer that contains one or more therapeutic agents. The therapeutic agents may be loaded into the biodegradable polymer in solution, precipitated in the biodegradable polymer, or chemically bound to the biodegradable polymer. The therapeutic agents will be released into the patient's eye when the biodegradable polymer hydrolyzes or dissolves.

The invention claimed is:

1. A device for delivery of therapeutic agents to the eye, comprising a polymeric structure containing one or more therapeutic agents that conforms to the curvature of a patient's outer eye and extends around the circumference of a patient's cornea.

2. A device for delivery of therapeutic agents to the eye comprising:
   a. a polymeric structure that conforms to the curvature of a patient's outer eye and extends around the circumference of a patient's cornea; and
   b. a barrier membrane containing one or more therapeutic agents.

3. The device of claim 2, wherein the barrier membrane runs along the entire bottom surface of the polymeric structure.

4. The device of claim 2, wherein the barrier membrane runs along a portion of the bottom surface of the polymeric structure.

5. The device of claim 1, wherein the polymeric structure contains one or more therapeutic agents that are precipitated in the polymer and that will dissolve to allow delivery of the agents into the eye.

6. The device of claim 2, wherein the polymeric structure contains one or more therapeutic agents that are precipitated in the polymer and that will dissolve to allow delivery of the agents into the eye.

7. A system of delivering therapeutic agents to the front of the eye comprising the device of claim 1.

8. A system of delivering therapeutic agents to the front of the eye comprising the device of claim 2.

9. A system of delivering therapeutic agents to the front of the eye comprising the device of claim 3.

10. A system of delivering therapeutic agents to the front of the eye comprising the device of claim 4.

11. A system of delivering therapeutic agents to the front of the eye comprising the device of claim 5.

12. A system of delivering therapeutic agents to the front of the eye comprising the device of claim 6.

* * * * *